US010456767B2

(12) United States Patent
Kawarai et al.

(10) Patent No.: US 10,456,767 B2
(45) Date of Patent: Oct. 29, 2019

(54) CYTOMETRIC MECHANISM, CELL CULTURE DEVICE COMPRISING SAME, AND CYTOMETRIC METHOD

(71) Applicant: Hitachi High-Technologies Corporation, Tokyo (JP)

(72) Inventors: Masako Kawarai, Tokyo (JP); Toshinari Sakurai, Tokyo (JP); Akihiro Shimase, Tokyo (JP); Hiroyuki Koshi, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 15/518,041

(22) PCT Filed: Oct. 22, 2014

(86) PCT No.: PCT/JP2014/078033
§ 371 (c)(1),
(2) Date: Apr. 10, 2017

(87) PCT Pub. No.: WO2016/063364
PCT Pub. Date: Apr. 28, 2016

(65) Prior Publication Data
US 2017/0306287 A1    Oct. 26, 2017

(51) Int. Cl.
*B01J 19/00* (2006.01)
*C12M 1/34* (2006.01)
(Continued)

(52) U.S. Cl.
CPC ......... *B01J 19/0006* (2013.01); *C12M 41/46* (2013.01); *C12M 41/48* (2013.01);
(Continued)

(58) Field of Classification Search
USPC ................................. 422/73; 436/10; 702/21
See application file for complete search history.

(56) References Cited

U.S. PATENT DOCUMENTS 3,758,787 A * 9/1973 Sigrist .................... G01N 21/53
356/339
4,286,876 A * 9/1981 Hogg ..................... G01N 21/47
250/574
(Continued)

FOREIGN PATENT DOCUMENTS

JP 02-500297 A 2/1990
JP 2012-143231 A 8/2012
(Continued)

OTHER PUBLICATIONS

International Search Report of PCT/JP2014/078033 dated Jan. 27, 2017.
(Continued)

*Primary Examiner* — Dean Kwak
(74) *Attorney, Agent, or Firm* — Mattingly & Malur, PC

(57) ABSTRACT

A cytometric mechanism includes: a flow path through which a cell suspension is made to flow; a liquid drive unit for sending the cell suspension which is in the flow path; and a computation unit for irradiating, with irradiation light from a light source, a cell suspension flowing through a flow cell, and for finding a cell survival rate in the cell suspension on the basis of a resulting forward scattered light intensity and transmittance and/or side scattered light intensity. The invention is provided with a calibration curve database for storing, in advance, respective calibration curves indicative of a relationship between viable cell concentration and forward scattered light intensity, a relationship between dead cell concentration and the transmittance, and a relationship between a cell survival rate and the side scattered light intensity.

4 Claims, 8 Drawing Sheets

(51) Int. Cl.
*C12M 1/36* (2006.01)
*C12M 1/00* (2006.01)
*G01N 15/06* (2006.01)
*G01N 21/53* (2006.01)
*G01N 33/483* (2006.01)
*G01N 33/50* (2006.01)
*G01N 15/00* (2006.01)

(52) U.S. Cl.
CPC ............ *C12M 47/02* (2013.01); *C12M 47/04* (2013.01); *G01N 15/06* (2013.01); *G01N 21/53* (2013.01); *G01N 33/4833* (2013.01); *G01N 33/5005* (2013.01); *G01N 2015/0065* (2013.01); *G01N 2015/0693* (2013.01); *G01N 2201/127* (2013.01)

(56) References Cited

U.S. PATENT DOCUMENTS

| | | | | |
|---|---|---|---|---|
| 4,595,291 A * | 6/1986 | Tatsuno | ............ | G01N 15/0211 356/336 |
| 4,676,641 A * | 6/1987 | Bott | ............ | G01N 15/0205 250/564 |
| 4,953,978 A * | 9/1990 | Bott | ............ | G01N 15/0211 356/336 |
| 5,047,963 A * | 9/1991 | Kosaka | ............ | G01N 15/147 356/336 |
| 5,445,939 A | 8/1995 | Anderson | | |
| 5,812,419 A * | 9/1998 | Chupp | ............ | G01N 35/1004 702/20 |
| 6,252,658 B1 * | 6/2001 | Togawa | ............ | G01N 15/0211 356/335 |
| 6,507,400 B1 * | 1/2003 | Pina | ............ | G01N 15/1456 356/338 |
| 6,646,742 B1 * | 11/2003 | Gangstead | ............ | G01N 15/1404 356/342 |
| 6,778,271 B2 * | 8/2004 | Watson | ............ | G01N 15/0211 356/336 |
| 6,859,276 B2 * | 2/2005 | Xu | ............ | G01N 15/0211 356/336 |
| 7,745,221 B2 * | 6/2010 | Butler | ............ | B01L 3/502761 422/504 |
| 7,758,811 B2 * | 7/2010 | Durack | ............ | C12N 5/0612 422/73 |
| 7,869,038 B2 * | 1/2011 | Jones | ............ | G01N 15/0205 356/335 |
| 8,634,072 B2 * | 1/2014 | Trainer | ............ | G01N 15/0205 356/335 |
| 9,770,713 B2 * | 9/2017 | Haga | ............ | G01N 21/6428 |
| 9,869,625 B2 * | 1/2018 | Spriggs | ............ | G01N 15/0211 |
| 2010/0273168 A1 | 10/2010 | Krockenberger et al. | | |
| 2011/0177544 A1 | 7/2011 | Takahashi et al. | | |
| 2011/0181869 A1 * | 7/2011 | Yamaguchi | ............ | G01N 15/0205 356/72 |
| 2012/0013727 A1 | 1/2012 | Breniman et al. | | |
| 2017/0159003 A1 * | 6/2017 | Shimase | ............ | C12M 27/00 |

FOREIGN PATENT DOCUMENTS

| | | | | |
|---|---|---|---|---|
| JP | 2012-525589 A | | 10/2012 | |
| JP | 2013-517460 A | | 5/2013 | |
| JP | 2014-148636 | * | 7/2014 | ............ C12M 41/40 |
| WO | 2009/157385 A1 | | 12/2009 | |

OTHER PUBLICATIONS

Japanese Office Action received in corresponding Japanese Application No. 2016-554992 dated Jan. 9, 2018.

* cited by examiner

[FIG. 1]
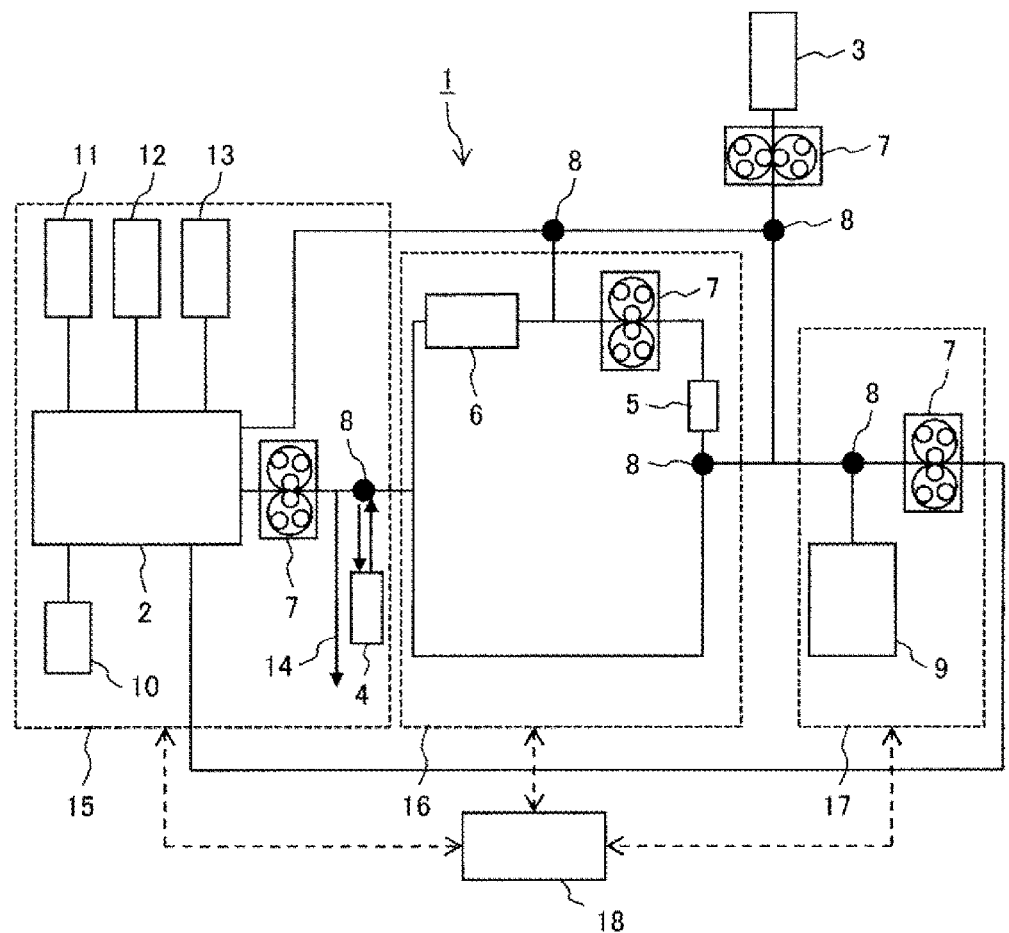
[FIG. 2]
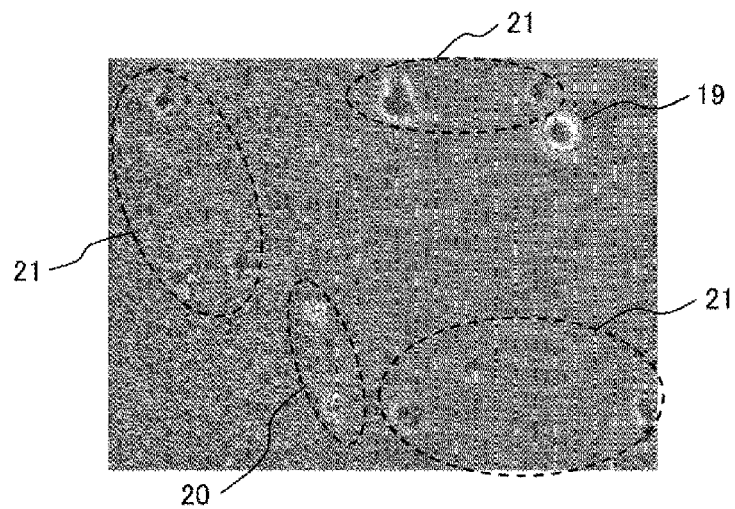

[FIG. 3]
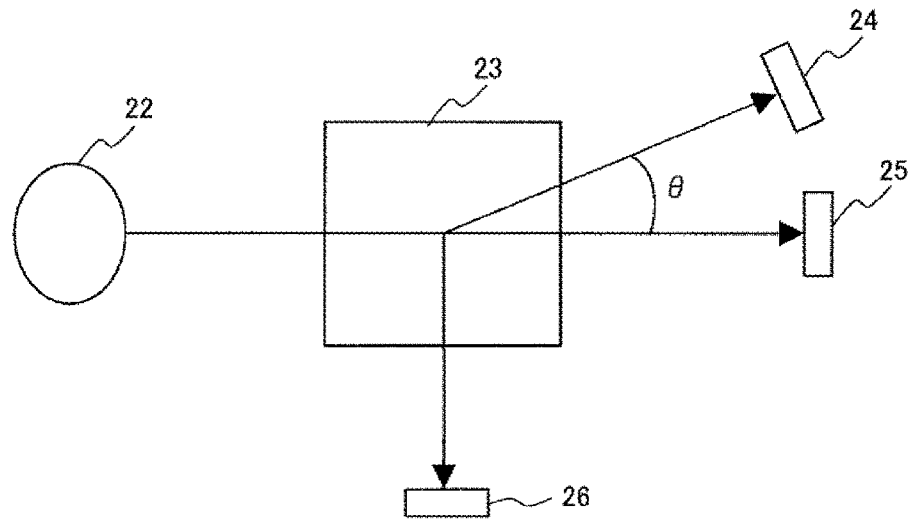
[FIG. 4]
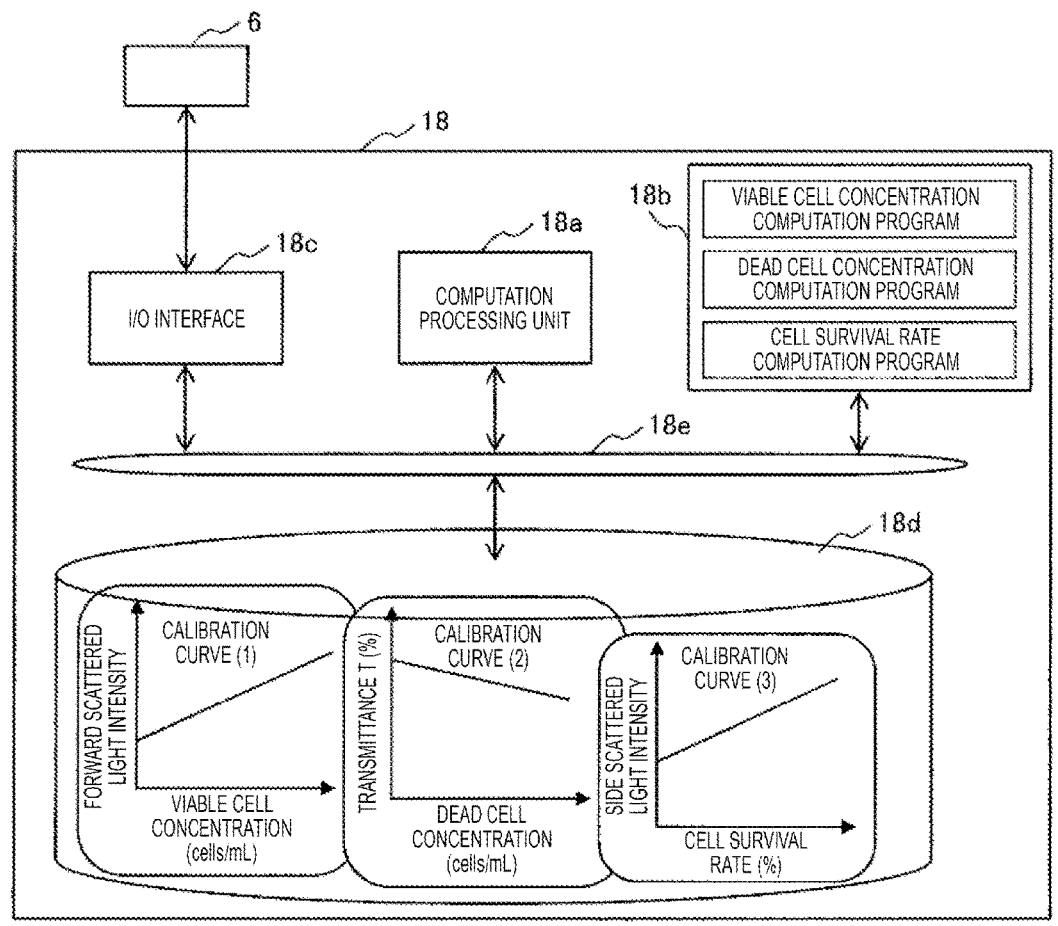

[FIG. 5]
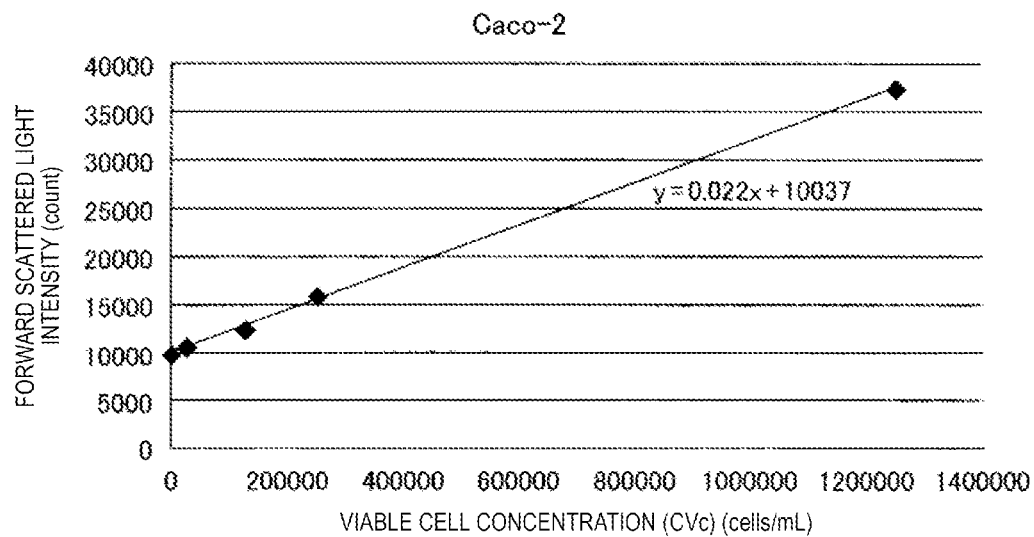
[FIG. 6]
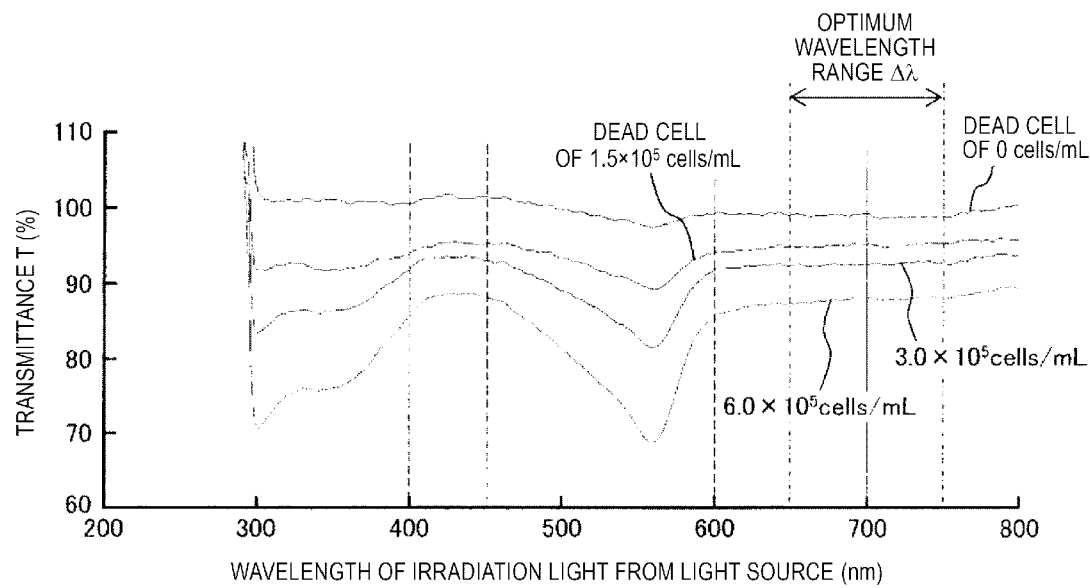

[FIG. 7]
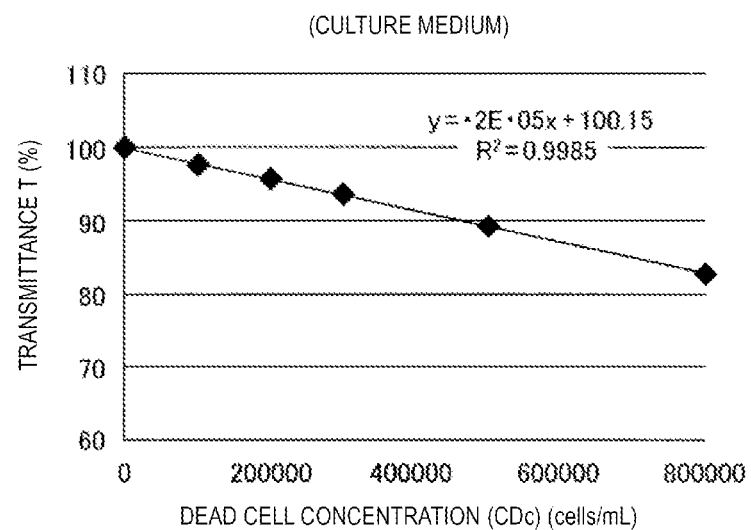
[FIG. 8]
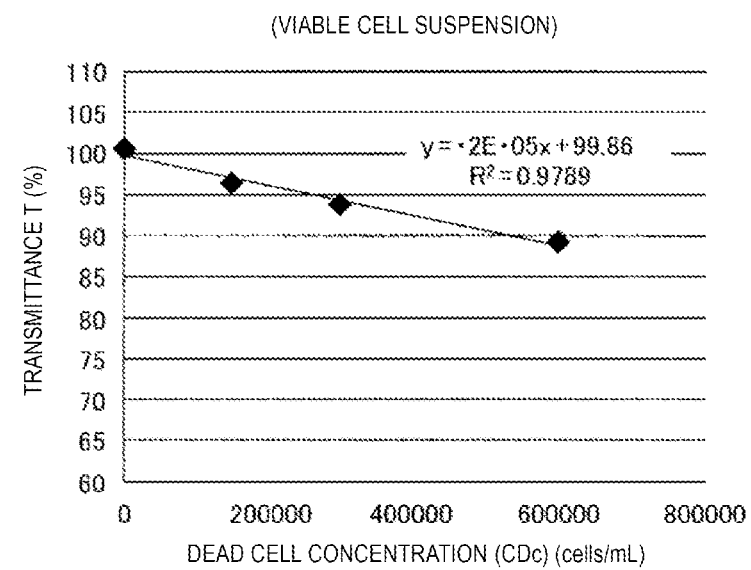

[FIG. 9]
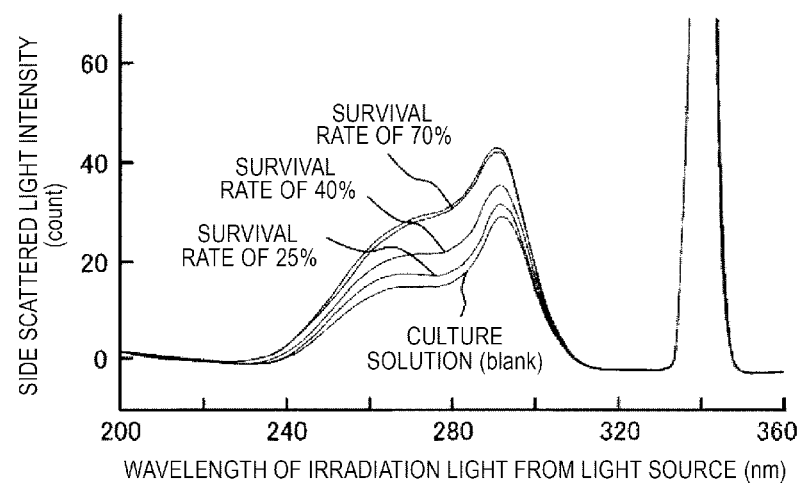
[FIG. 10]
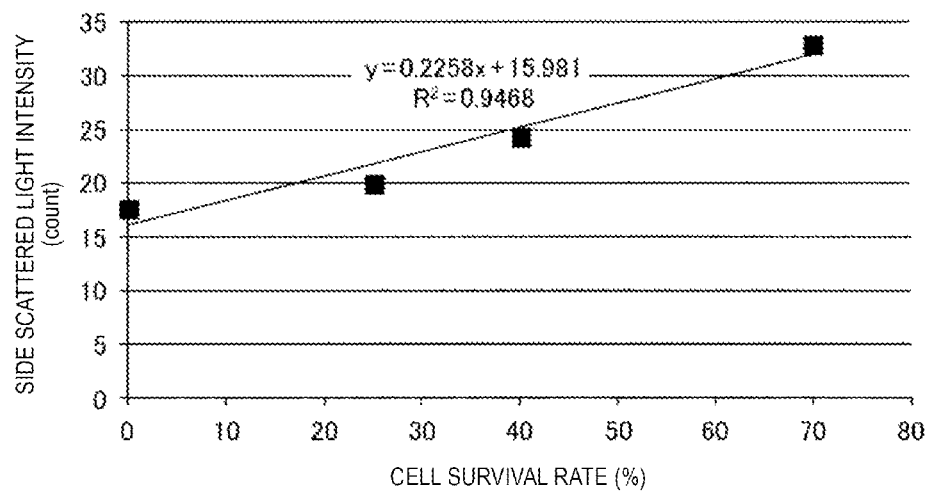

[FIG. 11]
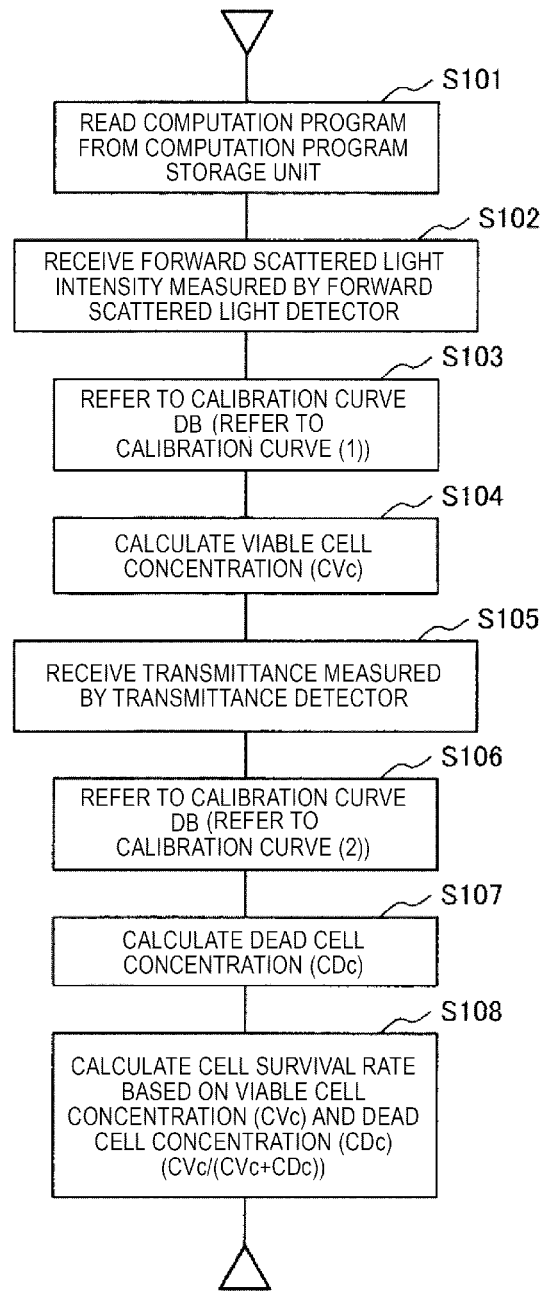

[FIG. 12]
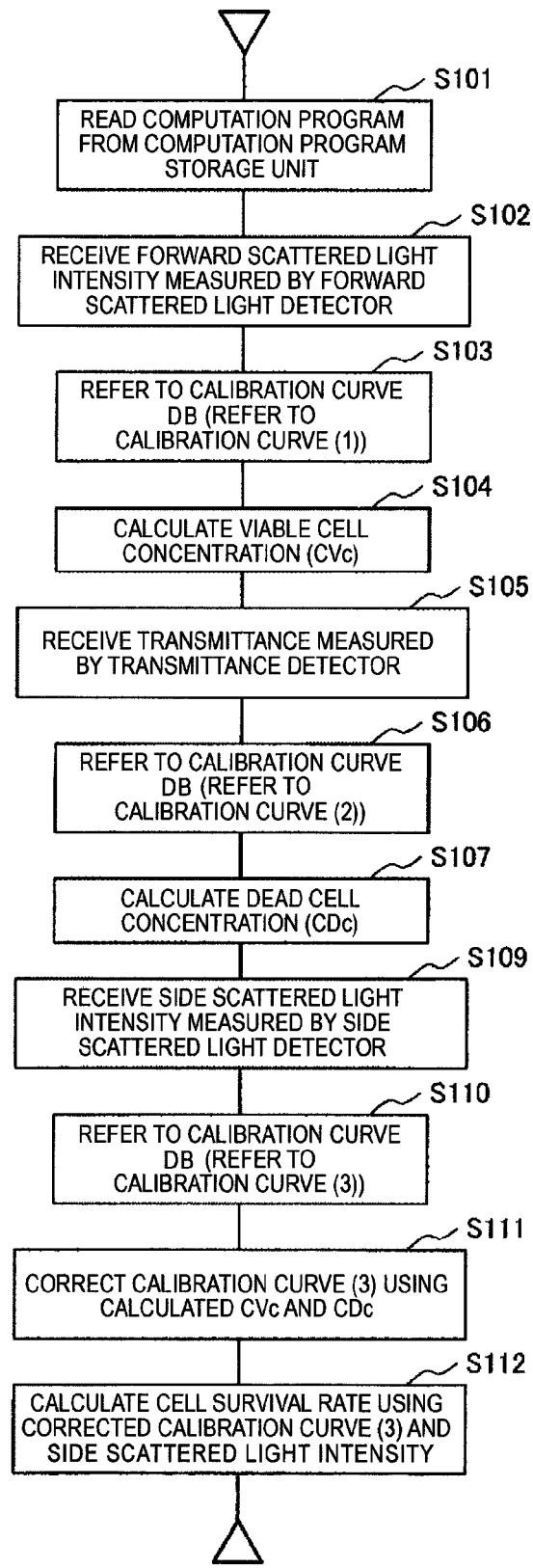

[FIG. 13]
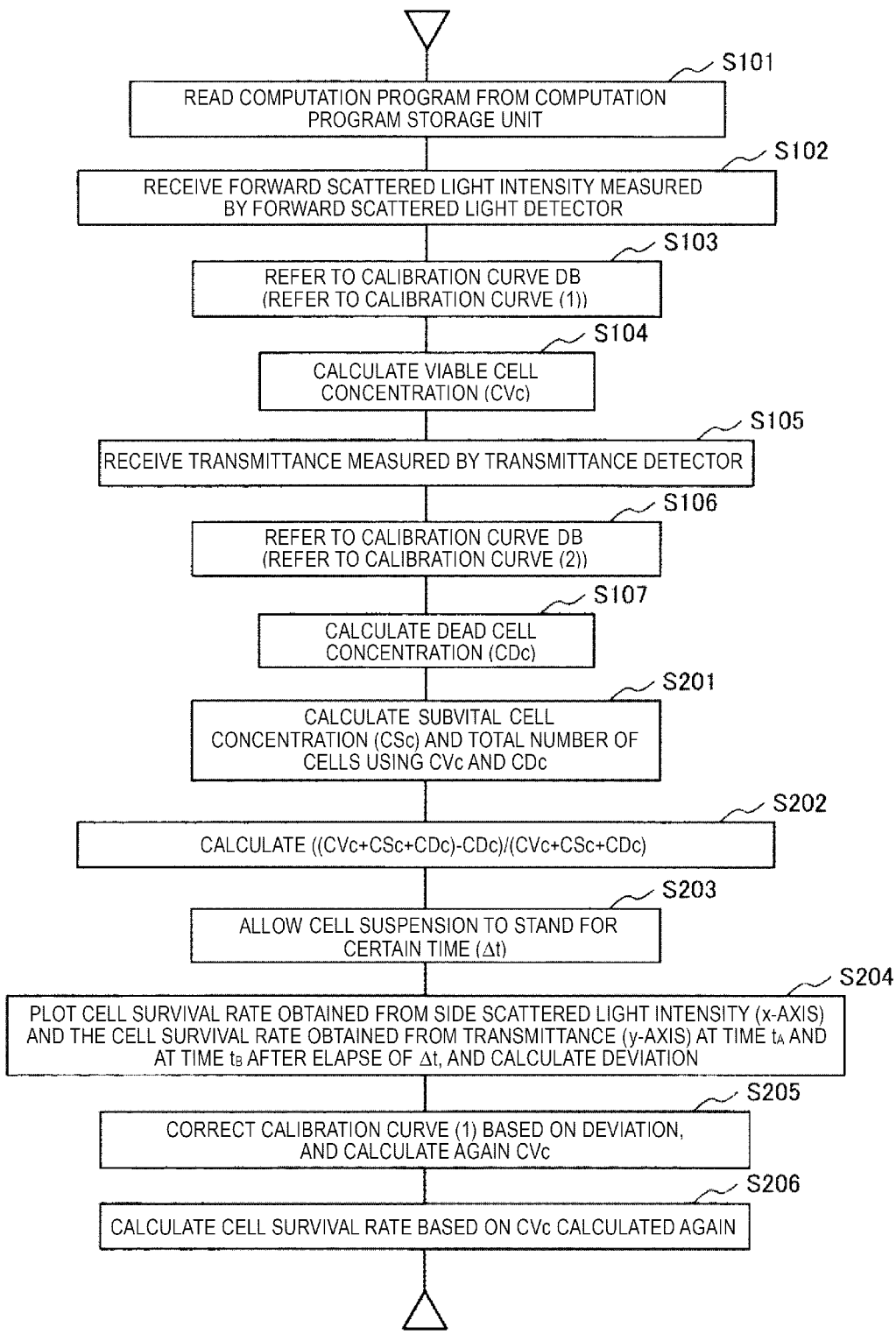

CYTOMETRIC MECHANISM, CELL CULTURE DEVICE COMPRISING SAME, AND CYTOMETRIC METHOD

TECHNICAL FIELD

The present invention relates to a cytometric mechanism, an automatic cell culture device including the same, and a cytometric method.

BACKGROUND ART

In the related art, in cell culture, most of operations are performed manually. However, since the cell culture operations are complicated and time-consuming, a great deal of human cost is required. In particular, since cell counting and cell survival rate measurement are complicated and difficult operations, a worker's skill level is essential.

Thus, as in a cell counter described in PTL 1, a method of automatically calculating a cell count, a cell survival rate, or the like based on image data of cultured cells which are stained with trypan blue, is proposed.

In addition, PTL 2 discloses a method of identifying and quantifying red blood cells, white blood cells, and platelets in whole blood by using a laser light source having a plurality of wavelengths and using a plurality of times of inflow optical measurements (flow cytometer).

CITATION LIST

Patent Literature

PTL 1: JP-T-2013-517460
PTL 2: JP-T-2012-525589

SUMMARY OF INVENTION

Technical Problem

When attempting to count the number of cells using the cell counter described in PTL 1, accuracy is improved compared with counting by a blood cell counter in the related art. However, according to experimental results by this applicant, the reliability of the counting result is extremely decreased at a concentration range in which a cell concentration in a cell suspension is $1 \times 10^5$ cells/mL or less and $5 \times 10^6$ cells/mL or more. In a case where a cell culture device is applied to regenerative medicine or cell therapy, it is necessary to measure a specimen having a cell concentration of $1 \times 10^5$ cells/mL or less. However, the cell counter according to PTL 1 cannot be applied to the measurement due to low measurement accuracy at the concentration range. In addition, although a cell survival rate is used to determine the life or death of a cell based on contrast in a contour of the cell, since a low-active cell (hereinafter, a subvital cell) has low contrast in the contour, it is difficult to determine the life or death of the cell. That is, in subculture, it is difficult to measure a cell survival rate in a cell suspension.

Further, in a cytometric method using the flow cytometer disclosed in PTL 2, since it is necessary to measure each cell, it takes a long time.

On the other hand, in the case of cell culture for the purpose of regenerative medicine or cell therapy, since safety is not confirmed, cells supplied for treatment cannot be stained. Thus, it is difficult to apply the cytometric method according to PTL 1 requiring cell staining with a pigment to such cell culture. Furthermore, as described above, in the cytometric method according to PTL 2, since it takes a long time for the measurement, it is difficult to apply the cytometric method to a cell culture device.

Therefore, the invention provides a cytometric mechanism, a cell culture device including the cytometric mechanism, and a cytometric method with which it is possible to measure at least a cell survival rate rapidly and at high accuracy, in a manner not dependent on a worker's skill level and without having to stain cultured cells.

Solution to Problem

In order to solve the problem, a cytometric mechanism according to the invention includes: a flow path through which a cell suspension is made to flow; a liquid drive unit that sends the cell suspension which is in the flow path; and a computation unit that irradiates, with irradiation light from a light source, the cell suspension flowing through the flow path, and that computes at least a cell survival rate in the cell suspension based on forward scattered light intensity and transmittance and/or side scattered light intensity which are obtained by the irradiation.

In addition, a cell culture device according to the invention includes a cytometric mechanism including an expansion culture mechanism that cultures and proliferates cells and separates the proliferated cells; a flow path through which a cell suspension including the cells separated by the expansion culture mechanism is made to flow; a liquid drive unit that sends the cell suspension which is in the flow path; and a computation unit that irradiates, with irradiation light from a light source, the cell suspension flowing through the flow path, and that calculates at least a cell survival rate in the cell suspension based on forward scattered light intensity and transmittance and/or side scattered light intensity which are obtained by the irradiation.

Further, a cytometric method according to the invention that computes at least a cell survival rate in a cell suspension, includes: a step of irradiating, with irradiation light from a light source, a cell suspension flowing through a flow cell, from a direction orthogonal to the flow of the cell suspension; a step of measuring the intensity of forward scattered light which is scattered from the cell suspension; a step of measuring transmittance of the irradiation light transmitted through the cell suspension; a step of computing a viable cell concentration in the cell suspension based on the measured forward scattered light intensity and a first calibration curve which is stored in advance and indicates the relationship between the viable cell concentration and the forward scattered light intensity; a step of computing a dead cell concentration in the cell suspension based on the measured transmittance and a second calibration curve which is stored in advance and indicates the relationship between the dead cell concentration and the transmittance; and a step of computing a cell survival rate in the cell suspension based on the computed viable cell concentration and the computed dead cell concentration.

Advantageous Effects of Invention

According to the invention, it is possible to provide a cytometric mechanism, a cell culture device including the cytometric mechanism, and a cytometric method with which it is possible to measure at least a cell survival rate rapidly and at high accuracy, in a manner not dependent on a worker's skill level and without having to stain cultured cells.

For example, it is possible to rapidly measure a cell survival rate in a cell suspension including subcultured cells in a flow cell disposed in a cell culture device without cell staining.

The objects, configurations, and effects other than those described above will be clarified from the description of the following embodiment.

BRIEF DESCRIPTION OF DRAWINGS

FIG. 1 is an overall configuration diagram of a cell culture device according to an embodiment of the invention.

FIG. 2 is a microscope image of Caco-2 cells, and is a diagram illustrating an image including viable cells, dead cells, and subvital cells.

FIG. 3 is a schematic configuration diagram of the optical system of a measurement unit illustrated in FIG. 1.

FIG. 4 is a schematic configuration diagram of a control unit illustrated in FIG. 1.

FIG. 5 is a diagram illustrating the relationship between a viable cell concentration and forward scattered light intensity in a Caco-2 cell suspension, and is an explanatory diagram of a calibration curve (1).

FIG. 6 is a spectrum diagram illustrating the relationship between a wavelength of irradiation light from a light source and transmittance T at each dead cell concentration in a Caco-2 cell suspension.

FIG. 7 is a diagram illustrating the relationship between a dead cell concentration and transmittance T in a Caco-2 culture medium, and is an explanatory diagram of a calibration curve.

FIG. 8 is a diagram illustrating the relationship between a dead cell concentration and transmittance T in a Caco-2 cell suspension, and is an explanatory diagram of a calibration curve (2).

FIG. 9 is a spectrum diagram illustrating the relationship between a wavelength of irradiation light from a light source and side scattered light intensity in a culture solution included in a Caco-2 cell suspension and at each cell survival rate.

FIG. 10 is a diagram illustrating the relationship between a cell survival rate and side scattered light intensity in a Caco-2 cell suspension, and is an explanatory diagram of a calibration curve (3).

FIG. 11 is a flowchart of cell survival rate calculation processing by a cytometric mechanism according to an example 1 as an example of the invention.

FIG. 12 is a flowchart of cell survival rate calculation processing by the cytometric mechanism according to an example 2 as another example of the invention.

FIG. 13 is a flowchart of cell survival rate calculation processing by the cytometric mechanism according to an example 3 as another example of the invention.

DESCRIPTION OF EMBODIMENTS

As a result of hard efforts, the present inventors found that, in the case of cultured cells (subcultured cells or the like) used in regenerative medicine or cell therapy, depending on the difference in cell activity or the culture state (subculture environment or the like) of each patient or subject, dead cells having a small particle diameter, and dying cells or subvital cells are mixed together. The present inventors obtained findings that, since these cells have different size from active viable cells, it is difficult to accurately compute the number of the viable cells or a cell survival rate by only scattered light obtained by, for example, irradiating, with irradiation light from a light source, a cell suspension flowing through a flow cell. From the findings, the inventors found that it is possible to rapidly obtain the number of cells or a cell survival rate with high accuracy by identifying the various cells having different sizes, that is, active viable cells, subvital cells, and dead cells by using forward scattered light intensity and transmittance or by using forward scattered light intensity, transmittance, and side scattered light intensity.

In the present specification, a viable cell in the cell suspension is expressed alone or together with Vc, viable cell concentration is expressed alone or together with CVc, a dead cell in the cell suspension is expressed alone or together with Dc, dead cell concentration is expressed alone or together with CDc, a subvital cell in the cell suspension is expressed alone or together with Sc, and subvital cell concentration is expressed alone or together with CSc.

FIG. 1 is an overall configuration diagram of a cell culture device according to an embodiment of the invention. In FIG. 1, a flow path through which a cell suspension is made to flow is represented by a solid line, and a signal line for transmitting and receiving a control signal or a measurement signal is represented by a dotted line. The cell culture device 1 is configured with an expansion culture mechanism 15 that cultures and proliferates cells and that separates the proliferated cells, a cytometric mechanism 16 that measures the cells separated by the expansion culture mechanism 15 by dispersing the cells, a cell seeding mechanism 17 that sends the cell suspension dispersed by the cytometric mechanism 16 to the expansion culture mechanism 15, and a control unit 18. As described later, the control unit 18 has a function of cooperating with the cytometric mechanism 16 and computing a cell survival rate or the like in the cell suspension based on forward scattered light intensity, transmittance, and side scattered light intensity that are measured. In this respect, the control unit 18 constitutes a part of the cytometric mechanism 16. The control unit 18 also has a function of controlling the expansion culture mechanism 15, the cytometric mechanism 16, and the cell seeding mechanism 17. In the following, although a configuration in which the control unit 18 has a function of computing a cell survival rate, viable cell concentration (CVc), and dead cell concentration (CDc) in the cell suspension will be described as an example, the configuration is not limited thereto. For example, a control computation unit having the function may be provided in the cytometric mechanism 16, or a control computation unit may be disposed in a measurement unit 6 to be described later.

The expansion culture mechanism 15 is stored in a $CO_2$ incubator which is not illustrated. Similarly, the cytometric mechanism 16 and the cell seeding mechanism 17 may also be configured to be stored in the $CO_2$ incubator. The inside of the flow path in the cell culture device 1 is maintained in an aseptic state in a closed system. During the operation of the cell culture device 1, air which is introduced into the flow path passes through, for example, a HEPA filter (not illustrated), and cell culture including a subculture operation and the like can be performed under an environment where an aseptic state is maintained.

The cells to be cultured in an expansion culture container 2 which constitutes the expansion culture mechanism 15 are introduced from a cell supply unit 10 using a liquid drive unit, for example, such as a syringe pump or the like. An appropriate amount of a cell culture solution is introduced from a culture solution supply unit 3 using a liquid drive unit, for example, a squeezing pump 7. The cell culture solution flows through three-way valves 8 and the flow path, and is supplied to the expansion culture container 2. Thereafter, the container is shaken such that the cells to be cultured in the expansion culture container 2 have a uniform concentration in the introduced cell culture solution, and then the cells are allowed to stand for several days. The cells to be cultured are cultured for several days in the expansion culture container 2 under appropriate conditions in the $CO_2$ incubator. A microscope is provided in the expansion culture container 2 so as to observe a proliferation state of the cultured cells. This is because there is a concern that, when the cultured cells are in a confluent state of 100%, that is, the cultured cells proliferate over the entire bottom surface of the expansion culture container 2, further proliferation cannot be made and the activity of the cultured cells may decrease or the cultured cells may be dead. Typically, the cultured cells are preferably separated at the time when the cultured cells reach a confluent state of 70% to 80%. The cell cleaning solution supply unit 11 contains a cleaning solution suitable for cells such as phosphate buffered sline (PBS) or 4-(2-hydroxyethyl)-1-piperazineethanesulfonic acid (HEPES) buffer solution. For example, a cleaning solution from the cell cleaning solution supply unit 11 is introduced into the expansion culture container 2 via a syringe pump, and thus the cell culture solution with a long retention period, and dead cells or dust and the like are extruded. The extruded cell culture solution including dead cells is discharged to the outside of the closed system of the cell culture device 1 via a squeezing pump 7, as a waste liquid 14. A cell separation solution supply unit 12 contains proteolytic enzymes such as trypsin, collagenase, or dispase. These proteolytic enzymes are introduced into the expansion culture container 2, and allowed to stand for a certain period of time. Proteins such as integrin that adhere the proliferated cultured cells to the bottom surface of the expansion culture container 2 are decomposed by these proteolytic enzymes, and thus the cultured cells are separated from the expansion culture container 2. A cell separation solution inhibitor supply unit 13 contains an enzyme activity inhibitor such as a trypsin inhibitor or a cell culture solution. The cell separation solution inhibitor is introduced into the expansion culture container 2, and thus the activity of the proteolytic enzymes is stopped after separation of the cultured cells. Therefore, damage to the cultured cells due to the activity of the enzymes can be reduced.

A sample introduction unit 4 collects the cultured cells separated from the bottom surface of the expansion culture container 2 via a squeezing pump 7 and a three-way valve 8. At this time, in a case where there are many residues of the cultured cells on the bottom surface of the expansion culture container 2, the cultured cells are cleaned by the cell culture solution introduced from the culture solution supply unit 3, and then collected into the sample introduction unit 4. Thus, it is possible to improve the collection rate of the cultured cells.

The cultured cells collected in the sample introduction unit 4 are introduced into a circulation flow path of the cytometric mechanism 16 via a liquid drive unit such as a syringe pump (not illustrated) and a three-way valve 8, as a cell suspension. The cytometric mechanism 16 is configured with a dispersion unit 5, a squeezing pump 7 as a liquid drive unit, and a measurement unit 6. The dispersion unit 5, the squeezing pump 7, and the measurement unit 6 are connected to the circulation flow path. Depending on the type of the cells to be cultured, the cohesiveness of the cells differs. Hence, in the case of culturing cells with high cohesiveness, the cultured cells included in the cell suspension that is introduced into the circulation flow path of the cytometric mechanism 16 (hereinafter, simply referred to as cells) flow in the circulation flow path in a lump shape. The cell suspension is introduced into the dispersion unit 5 via a three-way valve 8 by the squeezing pump 7 as a liquid drive unit, dispersed from the lump shape, and then introduced into the measurement unit 6. Here, the dispersion unit 5 is formed, for example, by providing a narrow portion at which the diameter of the flow path sharply decreases or a partition plate such as an orifice in the flow path. When the cell suspension flows through the narrow portion or the orifice, the lump-shaped cells are dispersed by shear force (shear stress). In the case of culturing cells with low cohesiveness, it is not always necessary to dispose the dispersion unit 5 in the cytometric mechanism 16, and the cytometric mechanism 16 may be configured by connecting the measurement unit 6, the squeezing pump 7, and the three-way valve 8 to the circulation flow path.

The cell seeding mechanism 17 includes a cell seeding sample adjustment unit 9 that is connected, via a three-way valve 8, to a flow path of which the one end is connected to the expansion culture container 2 and the other end is connected to the circulation flow path in the cytometric mechanism 16 via the three-way valve 8. The cell seeding sample adjustment unit 9 is disposed to adjust the cell concentration in the cell suspension flowing through the circulation flow path in the cytometric mechanism 16. That is, a squeezing pump 7 as a liquid drive unit is driven such that the cell concentration in the cell suspension becomes a desired cell concentration, and thus the cell suspension including the cells separated from the bottom surface of the expansion culture container 2 is taken into the cell seeding sample adjustment unit 9 via the flow path of which the one end is connected to the expansion culture container 2 and via the three-way valve 8. Thereafter, a desired amount of the cell culture solution is introduced into the cell seeding sample adjustment unit 9 from the culture solution supply unit 3 via the three-way valve 8 by driving of the squeezing pump 7, and the introduced cell culture solution is diluted by mixing with the cell suspension which is already taken into the cell seeding sample adjustment unit 9. The diluted cell suspension is sent to the circulation flow path of the cytometric mechanism 16, and the forward scattered light intensity, the transmittance, and the side scattered light intensity are measured by the measurement unit 6 to be described in detail later.

Here, viable cells (Vc), subvital cells (Sc), and dead cells (Dc) included in the cell suspension will be described. FIG. 2 illustrates a microscope image of Caco-2 cells that are human colon cancer cell strains. The microscope image illustrated in FIG. 2 is an image of Caco-2 cells obtained under the following conditions. The Caco-2 cells are obtained by culturing the cells in a confluent state of 100% or more and collecting the cells that are floating in the culture solution without separating the adhered cells. The activity of most of the cultured cells in this state decreases, some of the cells are separated, and many dead cells are floating in the cell culture solution. Apart of the cell culture solution is taken and the cell concentration and the survival rate are measured using a cell counter. As a result, the cell concentration is $5 \times 10^5$ cells/mL and the survival rate is 20%. This sample is dropped on a slide glass and fixed by a cover glass, and then the microscope image illustrated in FIG. 2 is obtained by capturing an image of the sample, with an objective lens having a magnification of 20, using an inverted microscope. As illustrated in FIG. 2, still active viable cells (Vc) 19, subvital cells (Sc) 20, dead cells (Dc) 21 without activity are observed. The viable cells (Vc) 19 shine white and have a large particle diameter, whereas the dead cells (Dc) 21 are colored entirely black and many dead cells are not in the form of particles. In addition, in the dead cell, it is observed that the cell membrane is unclear and the internal structure of the cell is changed. Even though the dead cells look large, since the dead cells are not in the form of particles, the dead cells are less likely to scatter light. Although the subvital cells (Sc) 20 shine white in an intermediate state between the viable cells (Vc) 19 and dead cells (Dc) 21, it can be seen that the particle diameter of the subvital cells is smaller than that of the viable cells (Vc) 19.

Although the viable cells (Vc), the subvital cells (Sc), and the dead cells (Dc) illustrated in FIG. 2 are Caco-2 cells, the difference in particle diameter depending on the cell type will be described here. The particle diameter of the viable cells (Vc) is approximately 10 μm in NIH/3T3 cells, is approximately 14 μm in the human colon cancer cell strains (Caco-2 cells) or human oral mucosal epithelial cells, and is approximately 20 μm in myoblasts of human skeletal muscles. In addition, the particle diameter of the viable cells is approximately 10 μm to 50 μm in human mesenchymal stem cells, and is approximately 10 μm in human cartilage cells.

Next, the measurement unit 6 that constitutes the cytometric mechanism 16 illustrated in FIG. 1 will be described. FIG. 3 illustrates a schematic configuration diagram of the optical system of the measurement unit 6. The measurement unit 6 according to the present embodiment includes a flow cell 23 in which the cell suspension flows, a light source 22 that is disposed so as to be orthogonal to the flow direction of the cell suspension flowing through the flow cell 23, and a transmittance detector 25 that is disposed so as to face the light source 22 with the flow cell 23 therebetween, that is, such that the light receiving surface of the detector faces the optical axis of the irradiation light irradiated from the light source. In addition, the measurement unit 6 includes a forward scattered light detector 24 that is disposed on the transmittance detector 25 side and is disposed at a predetermined angle θ (forward scattering detection angle) with respect to the optical axis of the irradiation light, and a side scattered light detector 26 that is disposed on an axis perpendicular to the optical axis of the irradiation light, of which the axis passes the substantial center of the flow cell 23, and that is disposed at a position separated from the flow cell 23 by a predetermined distance. Here, as the light source 22, for example, a laser light source, an LED light source, a tungsten lamp, a xenon lamp, or the like that is used in a spectrophotometer, a scattered light photometer, a fluorophotometer, a flow cytometer, a particle size distribution measuring device, or the like, can be used.

Here, the forward scattered light is light which is scattered in a forward direction with respect to the optical axis of the light source 22, and the particle size of the cell is reflected in the measured forward scattered light intensity. The angle formed by the forward scattered light and the optical axis, that is, the forward scattering detection angle θ depends on the particle diameter. Therefore, for example, the forward scattering detection angle θ is adjusted in advance and the forward scattered light detector 24 is disposed such that the particle diameter of the viable cells (Vc) for each cell type is optimized. In this way, when the intensity of the forward scattered light which is scattered at an angle appropriate for the particle diameter of the viable cells (Vc) according to the cell type is measured, in a case where the viable cells (Vc) have the same particle diameter, the scattered light intensity is proportional to the concentration (CVc) of the viable cells (Vc). For measurement of the forward scattered light, it is necessary to select a wavelength of the light source according to the sizes of the cells (viable cells (Vc)). When the wavelength is appropriate for the particle diameter of the cells, the forward scattered light intensity is likely to change depending on the cell concentration, and it is preferable to irradiate light having a long wavelength as the particle diameter of the cells is longer. Preferably, the irradiation light from the light source 22 is parallel light such as laser light.

In addition, the color of the inside of the cell changes to be blackish as the state of the cell changes from a high activity state to a low activity state, that is, in the process in which the viable cell (Vc) changes into the dead cell (Dc). Thus, as the content of the dead cells (Dc) in the cell suspension increases, the amount of light transmitted through the cell suspension decreases. Therefore, it is possible to obtain the concentration (CDc) of the dead cells (Dc) by measuring the transmittance by the transmittance detector 25. In the measurement of the transmittance, since absorption of all organic components in the cell suspension overlaps in a region near ultraviolet light, it is difficult to accurately evaluate only the dead cells (Dc). In addition, a pH indicator for pH determination such as phenol red is added in the cell culture solution which is introduced into the expansion culture container 2 from the culture solution supply unit 3 illustrated in FIG. 1. Thus, the cell culture solution is colored yellow to red, and the transmittance greatly decreases at wavelengths in the visible light region due to the influence of the color of the cell culture solution. In consideration of these facts, when the transmittance is detected by the transmittance detector 25 in a long wavelength region, it is possible to stably measure the concentration (CDc) of the dead cells (Dc) in the cell suspension without being influenced by interference components.

Furthermore, the viable cells (Vc) are different from the dead cells (Dc) in the granule density in the cell and the internal structure of the cell. The side scattered light is light which is detected at an angle of 90° with respect to the optical axis of the light source 22 as described above, and the density and form of the particles are reflected in the side scattered light. Therefore, the cell survival rate is reflected in the difference in the intensity of the side scattered light which is scattered by irradiating, with irradiation light, the substance in the cell. When a spectrum of the side scattered light in the cell suspension is measured, a gentle peak derived from a cytoplasmic organic component is detected in ultraviolet region (region near 230 nm to 310 nm), and when the wavelength of the side scattered light approaches a wavelength in the visible light region, as described above, the transmittance is influenced by the color of the cell culture solution. Therefore, it is preferable to measure the side scattered light depending on the particles in the cell, at a short wavelength in the ultraviolet region.

FIG. 4 illustrates a schematic configuration diagram of the control unit 18 illustrated in FIG. 1. As described above, in the present embodiment, as an example, a case where the control unit 18 has a function of cooperating with the cytometric mechanism 16 and computing the cell survival rate or the like in the cell suspension based on the forward scattered light intensity, the transmittance, and the side scattered light intensity that are measured, is described.

The control unit 18 includes a computation processing unit 18*a*, a computation program storage unit 18*b*, an I/O interface 18*c*, and a calibration curve database (DB), which are connected to each other via an internal bus 18*e*. The I/O interface 18*c* can receive the forward scattered light intensity measured by the forward scattered light detector 24 of the measurement unit 6, the transmittance measured by the transmittance detector 25 of the measurement unit 6, and the side scattered light intensity measured by the side scattered light detector 26 of the measurement unit 6, and transmit an emission command (irradiation timing or the like) of the irradiation light to the light source 22 of the measurement unit 6. In the computation program storage unit 18b, a viable cell concentration computation program, a dead cell concentration computation program, and a cell survival rate computation program are stored. In the calibration curve database 18d, a calibration curve (1) which is used for computing the viable cell concentration (CVc) and indicates the relationship between the viable cell concentration (CVc) and the forward scattered light intensity, is stored in advance. Similarly, a calibration curve (2) which is used for computing the dead cell concentration (CDc) and indicates the relationship between the dead cell concentration (CDc) and the transmittance T, is also stored in advance. In addition, a calibration curve (3) which is used for computing the cell survival rate and indicates the relationship between the cell survival rate and the side scattered light intensity, is also stored in advance. As a program stored in the computation program storage unit 18b, a viable cell concentration computation program, a dead cell concentration computation program, and a cell survival rate computation program may be incorporated into one program and the program may be stored.

The computation processing unit 18a is realized by, for example, a single CPU or a processor such as a plurality of CPUs connected in parallel. The specific processing by the computation processing unit 18a will be described later in the example below. The computation processing unit 18a reads the viable cell concentration computation program from the computation program storage unit 18b, receives the forward scattered light intensity which is input from the I/O interface 18c via the internal bus 18e, and executes the viable cell concentration computation program. The computation processing unit 18a computes the viable cell concentration (CVc) in the cell suspension using the calibration curve (1) by referring to the calibration curve database 18d. In addition, the computation processing unit 18a reads the dead cell concentration computation program from the computation program storage unit 18b, receives the transmittance T which is input from the I/O interface 18c via the internal bus 18e, and executes the dead cell concentration computation program. The computation processing unit 18a computes the dead cell concentration (CDc) in the cell suspension using the calibration curve (2) by referring to the calibration curve database 18d. Further, in a case where the number of the subvital cells (Sc) included in the cell suspension is infinitely small and negligible, the computation processing unit 18a computes the cell survival rate using the viable cell concentration (CVc) and the dead cell concentration (CDc).

In contrast, in a case where the number of the subvital cells (Sc) included in the viable cell suspension is not negligible, the computation processing unit 18a computes the viable cell concentration (CVc) and the dead cell concentration (CDc) in the same way, and executes the following processing. The computation processing unit 18a reads the cell survival rate computation program from the computation program storage unit 18b, receives the side scattered light intensity which is input from the I/O interface 18c via the internal bus 18e, and executes the cell survival rate computation program. The computation processing unit 18a further computes the cell survival rate based on the viable cell concentration (CVc) and the dead cell concentration (CDc) using the calibration curve (3) by referring to the calibration curve database 18d.

In this manner, the control unit 18 computes the cell survival rate in the cell suspension by using the forward scattered light intensity, the transmittance T and/or the side scattered light intensity that are measured by the measurement unit 6, and using the calibration curves (1) to (3) which are stored in advance in the calibration curve database 18d, and thus it is possible to rapidly execute at least the measurement of the cell survival rate with high accuracy without depending on a worker's skill level and without staining the cultured cells.

As described above, the cell culture device 1 according to the present embodiment can compute the number of the viable cells (Vc) and the number of the dead cells (Dc) by computing the viable cell concentration (CVc) and the dead cell concentration (CDc). In addition, for the subvital cells (Sc), it is also possible to compute the subvital cell concentration (CSc) and further the number of the subvital cells (Sc) by setting a predetermined threshold value in advance for the forward scattered light intensity obtained from the forward scattered light detector 24 and the transmittance T obtained from the transmittance detector 25. For the setting of the threshold value, an optimum threshold value can be obtained by preparing a standard sample having a known concentration in advance and measuring the forward scattered light intensity and the transmittance T of the standard sample.

Hereinafter, as an example, in the case of human colon cancer cell strains (Caco-2 cells), the calibration curves (1) to (3) which are stored in advance in the calibration curve database 18d will be described.

<Calibration Curve (1) Indicating Relationship Between Viable Cell Concentration (CVc) and Forward Scattered Light Intensity>

FIG. 5 is a diagram illustrating the relationship between the viable cell concentration and the forward scattered light intensity in a Caco-2 cell suspension, and is an explanatory diagram of the calibration curve (1). The calibration curve (1) illustrated in FIG. 5 is obtained in a case where the forward scattering detection angle θ illustrated in FIG. 3 is set to 20°.

First, a standard sample in which viable cells (Vc) are included in a Caco-2 cell suspension at a viable cell concentration (CVc) of 100%, and furthermore, a plurality of standard samples having different viable cell concentrations (CVc) are prepared. The forward scattering detection angle θ is adjusted to 20°, the standard samples having different viable cell concentrations (CVc) respectively are passed through the flow cell 23, and the forward scattered light intensity is measured by the forward scattering light detector 24. The viable cell concentration (CVc) is plotted on the horizontal axis, and the measured forward scattered light intensity is plotted on the vertical axis. The measured values of the forward scattered light intensity at each viable cell concentration (CVc) that are plotted are approximated by a straight line, and thus the calibration curve illustrated in FIG. 5 is created. The calibration curve is stored in the calibration curve database 18d illustrated in FIG. 4 as the calibration curve (1). In this embodiment, although the standard samples in which the viable cells (Vc) of Caco-2 cells are included at a plurality of viable cell concentrations (CVc) are prepared, the standard samples are not limited thereto. For example, the calibration curve (1) may be created, by preparing latex particles having the same particle diameter as that of the viable cells (Vc) of Caco-2 cells, preparing standard samples in which the latex particles are mixed into the cell culture solution at different concentrations, and respectively measuring the forward scattered light intensity in the same way described above.

<Calibration Curve (2) Indicating Relationship Between Dead Cell Concentration (CDc) and Transmittance T>

FIG. 6 is a spectrum diagram illustrating the relationship between the wavelength of the irradiation light from the light source and the transmittance T at each dead cell concentration in a Caco-2 cell suspension.

First, Caco-2 cells are introduced into the culture container, the cells floating in the cell culture solution without adhering to the bottom surface of the culture container are collected, and then the cells are allowed to stand for 10 minutes after stirring. Thereafter, the cells in the vicinity of the liquid surface are separated, and the separated cells are measured by a cell counter. Thus, the dead cells (Dc) having a particle diameter of approximately 5 μm are obtained at 83%. Standard samples of the cell suspension are prepared using the dead cells (Dc) such that the dead cell concentration (CDc) becomes $1.5 \times 10^5$ cells/mL to $6.0 \times 10^5$ cells/mL and the viable cell concentration (CVc) becomes $1.8 \times 10^6$ cells/mL, and the spectrum of the transmittance T at each dead cell concentration (CDc) is measured. As a result, as illustrated in FIG. 6, each spectrum at dead cell concentrations (CDc) of 0 cells/mL, $1.5 \times 10^5$ cells/mL, $3.0 \times 10^5$ cells/mL, and $6.0 \times 10^5$ cells/mL is obtained by plotting the wavelength of the irradiation light from the light source on the horizontal axis and plotting the transmittance T on the vertical axis.

As illustrated in the spectrum diagram of FIG. 6, in a wavelength range of 400 nm or less and a wavelength range of 450 nm to 600 nm, the transmittance T decreases greatly in the samples with any dead cell concentration (CDc). This is because, in the wavelength range of 400 nm or less, absorption by the cytoplasm occurs, and in the wavelength range of 450 nm to 600 nm, absorption by the coloring of the cell culture solution due to the addition of the pH indicator as described above occurs. An optimum wavelength range Δλ of 650 nm to 750 nm is preferably used, as a wavelength range in which absorption of the irradiation light by cells that are turned black at wavelengths other than the wavelength ranges, that is, dead cells (Dc) can be measured. The results obtained by measuring the transmittance T at a wavelength of 700 nm within the optimum wavelength range Δλ, are shown in the following table 1.

TABLE 1

| Dead Cell Concentration in Cell Suspension (cells/mL) | Transmittance T (%, wavelength of 700 nm) |
|---|---|
| 0 | 100.6 |
| 150000 | 96.5 |
| 300000 | 93.8 |
| 600000 | 89.3 |

As shown in Table 1, the transmittance T is 100.6% at a dead cell concentration (CDc) of 0 cells/mL in the cell suspension, the transmittance T is 96.5% at a dead cell concentration (CDc) of $1.5 \times 10^5$ cells/mL in the cell suspension, the transmittance T is 93.8% at a dead cell concentration (CDc) of $3.0 \times 10^5$ cells/mL in the cell suspension, and the transmittance T is 89.3% at a dead cell concentration (CDc) of $6.0 \times 10^5$ cells/mL in the cell suspension. From this, by making a sample (cell culture solution or the like) having a dead cell concentration (CDc) of 0 cells/mL flow through the flow cell 23, measuring the transmittance T in advance by the transmittance detector 25, and storing the measured value in the storage unit (not illustrated) as a baseline, at an irradiation light wavelength of 700 nm, the differences between the measured value of the transmittance T at each dead cell concentration (CDc) in the cell suspension and the baseline are obtained. Thus, it is possible to output a decrease in the transmittance T depending on the dead cells (Dc) in the cell suspension.

FIG. 7 illustrates the relationship between the dead cell concentration (CDc) and the transmittance T in a Caco-2 culture medium. In addition, FIG. 8 illustrates the relationship between the dead cell concentration (CDc) and the transmittance T in a Caco-2 cell suspension. In both of FIG. 7 and FIG. 8, as described above, calibration curves are created by setting the wavelength of the irradiation light to 700 nm, setting the transmittance T of a standard sample having a dead cell concentration (CDc) of 0 cells/mL as a baseline, and obtaining the differences between the transmittance T of the standard sample at each dead cell concentration (CDc) and the baseline. It is confirmed that the slope of the calibration curve in the culture medium and the slope of the calibration curve in the cell suspension are the same, and that the transmittance T is attenuated without being influenced by the cell suspension as the number of the black dead cells (Dc) increases. Thereby, the calibration curve illustrated in FIG. 8 that indicates the relationship between the dead cell concentration (CDc) and the transmittance T is stored in the calibration curve database 18d illustrated in FIG. 4, as the calibration curve (2). In this embodiment, although the standard samples in which the dead cells (Dc) of Caco-2 cells are included at a plurality of dead cell concentrations (CDc) are prepared, the standard samples are not limited thereto. For example, the calibration curve (2) may be created, by preparing black particles having the same particle diameter as that of the dead cells (Dc) of Caco-2 cells, preparing standard samples in which the black particles are mixed into the cell culture solution at different concentrations, and respectively measuring the transmittance T in the same way described above. Here, as the black particles, for example, magnetic particles, carbon black, or the like can be used.

<Calibration Curve (3) Indicating Relationship Between Cell Survival Rate and Side Scattered Light Intensity>

FIG. 9 is a spectrum diagram illustrating the relationship between the wavelength of the irradiation light from the light source and the side scattered light intensity in a cell culture solution included in a Caco-2 cell suspension and at each cell survival rate.

First, as standard samples of the cell suspension, a standard sample of the cell suspension having a cell survival rate of 0%, that is, a standard sample including only the cell culture solution (blank), a standard sample of the cell suspension having a cell survival rate of 25%, a standard sample of the cell suspension having a cell survival rate of 40%, and a standard sample of the cell suspension having a cell survival rate of 70% are prepared. The standard samples of the cell suspension at each cell survival rate are caused to flow through the flow cell 23, and the side scattered light intensity is measured by the side scattered light detector 26. As a result, as illustrated in FIG. 9, spectra are obtained at cell survival rates of 0% (including only the cell culture solution), 25%, 40%, and 70% by plotting the wavelength of the irradiation light from the light source on the horizontal axis and plotting the side scattered light intensity on the vertical axis.

As illustrated in the side scattered light spectrum diagram of FIG. 9, in the ultraviolet region (region near 230 nm to 310 nm), a difference in the side scattered light intensity with respect to the wavelength of the irradiation light occurs for each cell survival rate. However, at wavelengths other than the ultraviolet region, since there is no difference in the side scattered light intensity for each cell survival rate, it is difficult to identify each cell survival rate in the diagram. This is because, when the wavelength of the side scattered light approaches a wavelength in the visible light region as described above, the transmittance is influenced by the color of the cell culture solution. Therefore, it is preferable to measure the side scattered light depending on the particles in the cell, at a short wavelength in the ultraviolet region. The measurement results of the side scattered light intensity at a wavelength of 280 nm are shown in the following table 2.

TABLE 2

| Cell Survival Rate in Cell Suspension (%) | Specimen No. | Side Scattered Light Intensity (280 nm, count) |
|---|---|---|
| 0 | 1 | 17.48 |
| 25 | 1 | 19.76 |
| 40 | 1 | 24.31 |
| 70 | 1 | 32.85 |
| 70 | 2 | 32.33 |
| 70 | 3 | 32.14 |

As shown in Table 2, the side scattered light intensity is 17.48 at a cell survival rate of 0% in the cell suspension, the side scattered light intensity is 19.76 at a cell survival rate of 25% in the cell suspension, the side scattered light intensity is 24.31 at a cell survival rate of 40% in the cell suspension, and the side scattered light intensity is 32.85 at a cell survival rate of 70% in the cell suspension. Thereby, only the cell culture solution (a cell survival rate of 0%) is caused to flow through the flow cell 23, the side scattered light intensity is measured in advance by the side scattered light detector 26, and the measured value is stored in the storage unit (not illustrated), as a baseline. At an irradiation light wavelength of 280 nm, the differences between the side scattered light intensity at each cell survival rate in the cell suspension and the baseline are obtained, and thus it is possible to output an increase in the cell survival rate in the cell suspension. The present embodiment is not limited to a configuration in which the difference (increase) with respect to the baseline is output, and the side scattered light intensity measured by the side scattered light detector 26 may be output as it is.

FIG. 10 illustrates the relationship between the cell survival rate and the side scattered light intensity in a Caco-2 cell suspension. As described above, a calibration curve is created by setting the wavelength of the irradiation light to 280 nm, setting the side scattered light intensity of a standard sample having a cell survival rate of 0% (including only the cell culture solution) as a baseline, and obtaining the differences between the side scattered light intensity of the standard sample at each cell survival rate. The calibration curve is created and stored in the calibration curve database 18d illustrated in FIG. 4, as the calibration curve (3). As illustrated in FIG. 10, it can be confirmed that the side scattered light intensity is proportional to the cell survival rate.

As described above, according to the cytometric mechanism 16 and the cell culture device 1 of the present embodiment, it is possible to measure at least a cell survival rate rapidly and at high accuracy, in a manner not dependent on a worker's skill level and without having to stain cultured cells.

Further, in addition to the cell survival rate, it is possible to compute the viable cell concentration (CVc), the dead cell concentration (CDc), the number of the viable cells (Vc), and the number of the dead cells (Dc). Furthermore, for the subvital cells (Sc), it is also possible to compute the subvital cell concentration (CSc) and the number of the subvital cells (Sc) in the same manner.

Hereinafter, examples according to the invention will be described with reference to the drawings.

Example 1

The cell culture device 1 according to this example has a configuration similar to the configuration illustrated in FIG. 1, the measurement unit 6 of the cytometric mechanism 16 has a configuration similar to the configuration illustrated in FIG. 3, the control unit 18 has a configuration similar to the configuration illustrated in FIG. 4, and the overlapped description thereof will be omitted. In the following, as an example, a case where the control unit 18 has a function of cooperating with the cytometric mechanism 16 and computing the cell survival rate or the like in the cell suspension based on the forward scattered light intensity, the transmittance, and the side scattered light intensity that are measured, is described. However, the present example is not limited thereto, for example, a control computation unit having the above function may be provided in the cytometric mechanism 16, or a control computation unit may be disposed in the measurement unit 6 to be described later.

In the following, in an example in which the cultured cells are human colon cancer cell strains (Caco-2 cells), a case where the angle formed by the forward scattered light and the optical axis of the light source 22 illustrated in FIG. 3, that is, the forward scattering detection angle θ is adjusted in advance to 20° and the forward scattered light intensity is measured will be described as an example. As described above, the forward scattering detection angle θ depends on the particle diameter of the viable cells (Vc) according to the cell type. The forward scattering detection angle θ which is optimized for measurement of another cell type other than the Caco-2 cells can be adjusted within a range of approximately 5° to 45°.

FIG. 11 is a flowchart of the cell survival rate calculation processing by the cytometric mechanism 16 according to this example. First, the computation processing unit 18a illustrated in FIG. 4 reads the viable cell concentration computation program and the dead cell concentration computation program from the computation program storage unit 18b via the internal bus 18e (step S101).

In step S102, the computation processing unit 18a receives the forward scattered light intensity measured by the forward scattered light detector 24 of the measurement unit 6 via the I/O interface 18c and the internal bus 18e. Here, the received forward scattered light detection intensity is the intensity of the forward scattered light which is scattered forward by irradiating, with irradiation light from the light source 22, the cell suspension flowing through the flow cell 23, the cell suspension including the separated Caco-2 cells which are cultured and proliferated by the expansion culture mechanism 15.

In step S103, the computation processing unit 18a accesses the calibration curve database 18d, and refers to the calibration curve (1) illustrated in FIG. 5 indicating the relationship between the viable cell concentration (CVc) and the forward scattered light intensity in the Caco-2 cell suspension. The computation processing unit 18a calculates the viable cell concentration (CVc) by extracting the viable cell concentration (CVc) corresponding to the measured forward scattered light intensity using the calibration curve (1) (step S104).

Next, in step S105, the computation processing unit 18a receives the transmittance T measured by the transmittance detector 25 of the measurement unit 6 via the I/O interface 18c and the internal bus 18e. The computation processing unit 18a again accesses the calibration curve database 18d, and refers to the calibration curve (2) illustrated in FIG. 8 indicating the relationship between the dead cell concentration (CDc) and the transmittance Tin the Caco-2 cell suspension (step S106). The computation processing unit 18a calculates the dead cell concentration (CDc) by extracting the dead cell concentration (CDc) corresponding to the measured transmittance T using the calibration curve (2) (step S107). The forward scattered light intensity is a relative signal, whereas the transmittance T is a signal that can be handled as an absolute value. This is because, similarly to the creation of the calibration curve (2), even in the measurement, only the cell culture solution (equivalent to a cell survival rate of 0%) is caused to flow through the flow cell 23, the transmittance T measured at that time is stored in advance as a baseline, and thus the difference between the transmittance T obtained when the cell suspension is caused to flow through the flow cell 23 and the baseline, that is, a decrease in the transmittance T is output. In other words, the transmittance T obtained from the transmittance detector 25 is a signal after background correction (background noise removal) by reference light.

In step S108, the computation processing unit 18a computes the cell survival rate in the Caco-2 cell suspension by calculating (CVc/(CVc+CDc)) using the viable cell concentration (CVc) obtained in step S104 and the dead cell concentration (CDc) obtained in step S107.

In this example, the Caco-2 cells as the cultured cells are resistant to shear force (shear stress), are likely to maintain a high cell survival rate, and are less influenced by a decrease in activity due to shear force. Thus, it can be assumed that the viable cell concentration (CVc), the dead cell concentration (CDc) and the subvital cell concentration (CSc) in the Caco-2 cell suspension are in the following relationship.

subvital cell concentration $(CSc) \ll (CVc+CSc+CDc)$ $CDc \approx (CSc+CDc)$

As described above, in this example, based on the forward scattered light intensity and the transmittance that are obtained by irradiating, with the irradiation light from the light source, the cell suspension, it is possible to obtain the number of viable cells included in the cell suspension at an unknown concentration, that is, the cell survival rate. In addition to the cell survival rate, it is also possible to obtain the viable cell concentration (CVc), the dead cell concentration (CDc), the number of the viable cells (Vc), and the number of the dead cells (Dc).

According to this example, it is possible to measure at least a cell survival rate rapidly and at high accuracy, in a manner not dependent on a worker's skill level and without having to stain cultured cells.

Further, according to this example, transmitted light after correction of the baseline is obtained, and thus, with a simple configuration of the measurement unit, it is possible to obtain measurement accuracy similar to that of a double beam spectrophotometer.

Example 2

FIG. 12 is a flowchart of the cell survival rate calculation according to an example 2 as another example of the invention. This example is different from the example 1 in that the side scattered light intensity measured by the side scattered light detector 26 of the measurement unit 6 is used for calculating the cell survival rate. In the following, the description of the same configuration as that of the example 1 will be omitted.

As illustrated in FIG. 12, in step S101, the computation processing unit 18a further reads the cell survival rate computation program from the computation program storage unit 18b via the internal bus 18e, in addition to the viable cell concentration computation program and the dead cell concentration computation program. The subsequent steps S102 to S107 are executed in the same manner as in the example 1.

After calculation of the dead cell concentration (CDc) in step S107, the computation processing unit 18a receives the side scattered light intensity measured by the side scattered light detector 26 of the measurement unit 6 via the I/O interface 18c and the internal bus 18e (step S109).

In step S110, the computation processing unit 18a accesses the calibration curve database 18d, and refers to the calibration curve (3) illustrated in FIG. 10 indicating the relationship between the cell survival rate and the side scattered light intensity in the Caco-2 cell suspension.

In step S111, the computation processing unit 18a corrects a y-intercept of the referenced calibration curve (3) using the viable cell concentration (CVc) obtained in step S104 and the dead cell concentration (CDc) obtained in step S107. Specifically, a cell suspension having a cell survival rate of approximately 100% is prepared in advance by using cells (in this case, Caco-2 cells) of an actual sample. Then, the relationship between the viable cell concentration (CVc) and the side scattered light intensity in the cell suspension is measured and obtained by the forward scattered light detector 24 and the side scattered light detector 26. The cell suspension having a cell survival rate of approximately 100% can be obtained by removing dirt and small dead cells in the suspension using a centrifugation operation. However, as in specimens which are used for regenerative medicine or cell therapy or primary cultured cells which are not established, depending on the cell type, the activity of the cells is likely to decrease due to damage in the process of a cell separation operation or a centrifugation operation, and the cell suspension may not maintain a cell survival rate of approximately 100%. In this case, an average maximum cell survival rate of the cell suspension obtained by the cell separation operation or the centrifugation operation is obtained. For example, in human oral mucosal epithelial cells, the maximum cell survival rate is approximately 85% to 90%. The relationship between the viable cell concentration (CVc) and the side scattered light intensity at the maximum cell survival rate is obtained and stored in the storage unit. The side scattered light intensity at the maximum cell survival rate is obtained based on the viable cell concentration (CVc) and the dead cell concentration (CDc) that are obtained in step S104 and step S107, using the relationship between the viable cell concentration (CVc) and the side scattered light intensity at the maximum cell survival rate. The y-intercept of the calibration curve (3) is corrected using a value of the obtained side scattered light intensity.

Next, in step S112, the computation processing unit 18a calculates the cell survival rate by extracting the cell survival rate corresponding to the measured side scattered light intensity using the corrected calibration curve (3) (step S112). The calibration curve (3) which is already stored in the calibration curve database 18d is replaced by the calibration curve (3) in which the y-intercept is corrected in step S111, and the corrected calibration curve (3) is stored. That is, the calibration curve (3) is updated to the corrected calibration curve (3) and the updated calibration curve (3) is stored.

Even in this example, similarly to the example 1, the Caco-2 cells as the cultured cells are resistant to shear force (shear stress), are likely to maintain a high cell survival rate, and are less influenced by a decrease in activity due to shear force. Thus, it is assumed that the viable cell concentration (CVc), the dead cell concentration (CDc) and the subvital cell concentration (CSc) in the Caco-2 cell suspension are in the following relationship.

subvital cell concentration(CSc)<<(CVc+CSc+CDc)

CDc≈(CSc+CDc)

According to this example, in addition to the effect of the example 1, the cell survival rate is calculated by the corrected calibration curve (3), and thus it is possible to measure the cell survival rate with higher accuracy.

Example 3

FIG. 13 is a flowchart of the cell survival rate calculation according to an example 3 as another example of the invention. In the example 1 and example 2, a case where the subvital cell concentration (CSc) in the cell suspension is small enough to be negligible, that is, a case where it can be assumed that CDc≈(CSc+CDc) is described. This example is different from the example 1 and the example 2 in that the cell survival rate in the cell suspension is calculated in a case where cannot be assumed that CDc≈(CSc+CDc). In the following, the description of the same configuration as those of the example 1 and the example 2 will be omitted.

Generally, the particle diameter of subvital cells (Sc) in a cell suspension sample is smaller than the particle diameter of viable cells (Vc) and larger than the particle diameter of dead cells (Dc). Thus, even when the particle diameter of the subvital cells (Sc) is substantially the same as the particle diameter of the dead cells (Dc), there is no influence on the calibration curve (1) which is used for calculating the viable cell concentration (CVc). However, in a case where, in the cell suspension, there are many subvital cells (Sc) having a particle diameter close to the particle diameter of the viable cells (Vc), the slope of the calibration curve (1) is influenced by the subvital cells.

As illustrated in FIG. 13, the computation processing unit 18a executes steps S101 to S107 in the same manner as in the example 1. Thereafter, the computation processing unit 18a calculates the subvital cell concentration (CSc) and the total number of the cells, that is, the number of the viable cells (Vc)+the number of the dead cells (Dc)+the number of the subvital cells (Sc) (step S201) based on the viable cell concentration (CVc) obtained in step S104 and the dead cell concentration (CDc) obtained in step S107.

In step S202, the computation processing unit 18a calculates the following (step S202).

((CVc+CSc+CDc)−CDc)/(CVc+CSc+CDc)

Then, the computation processing unit 18a compares the calculation result with CVc/(CVc+CDc) (similar to step S108 illustrated in FIG. 11). When there is a large difference in the comparison result, it is determined that there are many subvital cells (Sc) having a particle diameter close to the particle diameter of the viable cells (Vc) in the cell suspension. In addition, it is found that the viable cell concentration (CVc) which is calculated using the calibration curve (1) in step S104 is not a normal value. Thus, the process transitions to processing for correcting the calibration curve (1).

First, in step S203, the cell suspension is allowed to stand for a certain time (Δt). During a period of Δt, a part of the subvital cells (Sc) becomes dead cells (Dc), and the number of the subvital cells (Sc) decreases from the number at a time $t_A$ before the standing for Δt to the number at a time $t_B$ after the elapse of Δt. In addition, the number of the dead cells (Dc) increases from the number at a time $t_A$ before the standing for Δt to the number at a time $t_B$ after the elapse of Δt.

In step S204, the computation processing unit 18a sets the cell survival rate obtained from the side scattered light intensity as an x-axis, sets the cell survival rate obtained from the transmittance T as a y-axis, and plots the cell survival rates at the time $t_A$ and the time $t_B$. The slope of the straight line connecting the plotted two points is "1" in a case where the subvital cell concentration (CSc) is "0". However, the actual slope of the straight line deviates from "1". Therefore, the deviation caused by the subvital cells (Sc), that is, the difference in the slope of the straight line is calculated as a deviation.

In step S205, the computation processing unit 18a corrects the calibration curve (1) stored in the calibration curve database 18d using the deviation obtained in step S204, and calculates the viable cell concentration (CVc) by again extracting the viable cell concentration (CVc) corresponding to the measured forward scattered light intensity using the corrected calibration curve (1). The calibration curve (1) which is already stored in the calibration curve database 18d is replaced by the corrected calibration curve (1) in step S205, and the corrected calibration curve (1) is stored. That is, the calibration curve (1) is updated to the corrected calibration curve (1) and the updated calibration curve (1) is stored.

In step S206, the computation processing unit 18a calculates the cell survival rate by the following expression based on the viable cell concentration (CVc) calculated in step S205 and the dead cell concentration (CDc) obtained in step S107.

(CVc+CSc)/(CVc+CSc+CDc)

According to this example, in addition to the effect of the example 1, it is possible to obtain the cell survival rate with high accuracy even in a case where there are many subvital cells (Sc) in the cell suspension.

Instead of step S205 in this example, the forward scattering detection angle θ may be changed based on the deviation obtained in step S204, and the arrangement position of the forward scattered light detector 24 may be adjusted such that the changed forward scattering detection angle θ matches with the slope of the calibration curve (1) stored in the calibration curve database 18d.

In addition, in advance, latex particles having a particle diameter smaller than the particle diameter of the viable cells (Vc) are prepared, and the latex particles are added to the standard samples which are used in the creation of the calibration curve (1), as pseudo subvital cells (Sc). Then, the influence on the calibration curve (1) is obtained, the calibration curve (1) indicating the relationship between the viable cell concentration (CVc) and the forward scattered light intensity and being stored in the calibration curve database 18d. By creating a calibration curve when the latex particles are added to the standard samples at different concentrations and newly storing the calibration curve in the calibration curve database 18d, in a case where there are many subvital cells (Sc) in the cell suspension, the newly stored calibration curve may be used for calculating the viable cell concentration (CVc). In this case, the particle diameter of the latex particles to be used is preferably set to the particle diameter of the viable cells (Vc)±several μm, and it is preferable to use the latex particles having at least one kind of particle diameters.

In the example 1 to the example 3, although Caco-2 cells are described as an example of cultured cells, the invention can be also applied in the same manner in the case of culturing other various types of cells, for example, NIH/3T3 cells, human oral mucosal epithelial cells, myoblasts of human skeletal muscles, human mesenchymal stem cells, or human cartilage cells.

The invention is not limited to the above-described examples, and includes various modification examples. For example, the examples have been described in detail in order to explain the invention in an easy-to-understand manner, and are not necessarily limited to those having all the configurations described. In addition, a part of the configuration of one example can be replaced by the configuration of another example, and the configuration of another example can be added to the configuration of one example. Further, a part of the configuration of each example can be added, deleted, or replaced to, from, and by the configuration of another example.

REFERENCE SIGNS LIST

1: cell culture device
2: expansion culture container
3: culture solution supply unit
4: sample introduction unit
5: dispersion unit
6: measurement unit
7: squeezing pump
8: three-way valve
9: cell seeding sample adjustment unit
10: cell supply unit
11: cell cleaning solution supply unit
12: cell separation solution supply unit
13: cell separation solution inhibitor supply unit
14: waste liquid
15: expansion culture mechanism
16: cytometric mechanism
17: cell seeding mechanism
18: control unit
18a: computation processing unit
18b: computation program storage unit
18c: I/O interface
18d: calibration curve database (DB)
18e: internal bus
19: viable cell
20: subvital cell
21: dead cell
22: light source
23: flow cell
24: forward scattered light detector
25: transmittance detector
26: side scattered light detector

The invention claimed is:

1. A cell culture device comprising:
an expansion culture mechanism including an expansion culture container to receive cells to be cultured from a cell supply and a cell culture solution from a cell culture solution supply to culture and proliferate the cells, and to receive cell separation solution from a cell separation solution supply to separate the proliferated cells, the expansion culture mechanism further including a sample introduction unit to collect the separated cells; and a cytometric mechanism including
a circulation flow path coupled with the expansion culture mechanism and through which a cell suspension including the cells separated by the expansion culture mechanism is made to flow from the sample introduction unit to the circulation flow path, the circulation flow path forming a closed circulation loop;
a pump coupled with the circulation flow path to drive the cell suspension which is in the circulation flow path around the closed circulation loop;
a measurement unit disposed in the circulation flow path, the measurement unit including
a flow cell through which the cell suspension is made to flow;
a light source that is disposed so as to be orthogonal to the flow direction of the cell suspension flowing through the flow cell;
a transmittance detector that is disposed so as to face the light source with the flow cell therebetween and is disposed on the optical axis of the irradiation light from the light source;
a forward scattered light detector that is disposed on the transmittance detector side and is disposed at a predetermined angle with respect to the optical axis of the irradiation light according to a particle diameter of the viable cells; and
a side scattered light detector that is disposed so as to be orthogonal to the flow direction of the cell suspension and the optical axis of the irradiation light; and a control unit having a memory and a control processor programmed to
control the light source to irradiate, with irradiation light from the light source, the cell suspension flowing through the circulation flow path, and to calculate at least a cell survival rate in the cell suspension based on forward scattered light intensity and transmittance and side scattered light intensity which are obtained by the irradiation,
store a calibration curve database that stores, in advance, a first calibration curve indicating the relationship between a viable cell concentration of viable cells and the forward scattered light intensity, a second calibration curve indicating the relationship between a dead cell concentration and the transmittance, and a third calibration curve indicating the relationship between a cell survival rate and the side scattered light intensity;
compute the viable cell concentration in the cell suspension based on the forward scattered light intensity measured by the forward scattered light detector and the first calibration curve,
compute the dead cell concentration based on the transmittance measured by the transmittance detector and the second calibration curve,
correct the third calibration curve based on the computed viable cell concentration and the computed dead cell concentration, and
compute the cell survival rate in the cell suspension based on the corrected third calibration curve and the side scattered light intensity measured by the side scattered light detector.

2. The cell culture device according to claim 1,
wherein the forward scattered light detector is disposed within an angle range of approximately 5° to 45° with respect to the optical axis of the irradiation light, and
wherein the control unit is programmed to compute the viable cell concentration or the number of the viable cells in the cell suspension based on the forward scattered light intensity measured by the forward scattered light detector and the first calibration curve.

3. The cell culture device according to claim 1,
wherein the transmittance measured when only a cell culture solution flows through the flow cell is stored in advance as a baseline, and the transmittance measured when the cell suspension flows through the flow cell is output as a difference from the baseline, the cell suspension being obtained from the cell culture solution including cultured cells.

4. The cell culture device according to claim 1, further comprising:
a cell mechanism including a cell sample adjustment unit connected via a three-way valve to the expansion culture container to receive the cell culture solution and to the circulation flow path of the cytometric mechanism to receive the cell suspension so as to dilute the cell suspension by mixing with the cell culture solution so as to adjust a cell concentration in the cell suspension;
wherein the control unit is programmed to control the three-way valve to send the diluted cell suspension from the cell sample adjustment unit to the measurement unit via the circulation flow path of the cytometric mechanism for light detection and measurement.

* * * * *